US007655217B2

(12) United States Patent
Licha et al.

(10) Patent No.: US 7,655,217 B2
(45) Date of Patent: *Feb. 2, 2010

(54) NEAR INFRARED IMAGING AGENT

(75) Inventors: Kai Licha, Berlin (DE); Björn Riefke, Berlin (DE); Wolfhard Semmler, Glienicke (DE); Ulrich Speck, Berlin (DE); Christoph-Stephan Hilger, Berlin (DE)

(73) Assignee: Institut fur Diagnosikforschung GmbH, Berlin (DE)

( * ) Notice: Subject to any disclaimer, the term of this patent is extended or adjusted under 35 U.S.C. 154(b) by 201 days.

This patent is subject to a terminal disclaimer.

(21) Appl. No.: 11/387,367

(22) Filed: Mar. 22, 2006

(65) Prior Publication Data
US 2006/0165599 A1 Jul. 27, 2006

Related U.S. Application Data

(60) Continuation of application No. 11/093,082, filed on Mar. 29, 2005, now abandoned, which is a division of application No. 10/368,997, filed on Feb. 19, 2003, now Pat. No. 6,913,743, which is a continuation of application No. 10/180,272, filed on Jun. 26, 2002, now Pat. No. 6,926,885, which is a continuation of application No. 09/850,660, filed on May 7, 2001, now Pat. No. 7,025,949, which is a division of application No. 09/518,947, filed on Mar. 6, 2000, now Pat. No. 6,258,340, which is a continuation of application No. 08/849,369, filed on Nov. 7, 1997, now Pat. No. 6,083,485.

(51) Int. Cl.
*A61B 10/00* (2006.01)
*A61B 5/00* (2006.01)
*A61B 8/00* (2006.01)
(52) U.S. Cl. .............. 424/9.6; 424/1.11; 424/1.65; 424/9.1
(58) Field of Classification Search .......... 424/1.11, 424/1.65, 1.49, 1.73, 1.69, 9.1, 9.2, 9.3, 9.4, 424/9.5, 9.6, 9.7, 9.8; 548/100, 146, 215, 548/300.1, 400
See application file for complete search history.

(56) References Cited

U.S. PATENT DOCUMENTS

| 4,945,239 | A | | 7/1990 | Wist et al. | |
|---|---|---|---|---|---|
| 5,298,379 | A | | 3/1994 | Adin et al. | |
| 5,880,287 | A | * | 3/1999 | Dandliker et al. | 548/156 |
| 6,083,485 | A | * | 7/2000 | Licha et al. | 424/9.6 |
| 6,258,340 | B1 | * | 7/2001 | Licha et al. | 424/9.6 |
| 6,329,531 | B1 | * | 12/2001 | Turner et al. | 548/455 |
| 6,913,743 | B2 | * | 7/2005 | Licha et al. | 424/9.6 |
| 6,926,885 | B2 | * | 8/2005 | Licha et al. | 424/9.6 |
| 7,025,949 | B2 | * | 4/2006 | Licha et al. | 424/9.6 |

FOREIGN PATENT DOCUMENTS

| BE | 709463 | 7/1968 |
|---|---|---|
| DE | 2910760 | 4/1980 |
| DE | 3828360 | 2/1990 |
| DE | 3912046 | 3/1990 |
| DE | 4136769 | 5/1993 |
| DE | 4323368 | 1/1995 |
| WO | WO 8404665 | 9/1985 |
| WO | WO 8910758 | 11/1989 |
| WO | WO 9118006 | 11/1991 |
| WO | WO 9200748 | 1/1992 |
| WO | WO 9010219 | 5/1992 |

OTHER PUBLICATIONS

Golub et al., Science, Oct. 15, 1999, pp. 531-537.*
Dox et al (1993), The Harper Collins Illustrated Medical Dictionary, p. 132.*
Bonnett, "New photosensitisers for the photodynamic therapy of tumours," *SPIE*, vol. 2078, pp. 1-17, 1994.
Benaron, "Optical imaging reborn with technical advances," *Diagnostic Imaging*, pp. 69-76, 1994.
Folli, "Antibody-Indocyanin Conjugates for Immunophotodetection of Human Squamous Cell Carcinoma in Nude Mice," *Cancer Research*, vol. 54, pp. 2643-2649, 1994.
Mujumdar et al., "Cyanine Dye Labeling Reagents: Sulfoindocyanine Succinimidyl Esters," *Bioconjugate Chemistry*, vol. 4, No. 2, pp. 105-111, 1993.
Terpetschnig et al., "Synthesis, spectral properties and photostabilities of symmetrical and unsymmetrical squaraines; a new class of fluorophores with long-wavelength excitation and emission," *Analytica Chimica Acta*, vol. 282,pp. 633-641, 1993.
Terpetschnig et al., "An investigation of Squaraines as a New Class of Fluorophores with Long-Wavelength Excitation, and Emission," *Journal of Fluorescence*, vol. 3, No. 3, p. 153, 1993.
Büttner et al., "Laser-Mammographie mit NIR-Licht, " *Gynäkol Geburtshilfiche Rundsch*, vol. 33 (Suppl 1), pp. 299-300, 1993.
Googe et al., "Intraoperative Fluorescein Angiography," *Ophthalmology*, vol. 100, No. 8, pp. 1167-1170, 1993.
Henschen et al., "Determination of Plasma Volume and Total Blood Volume Using Indocyanine Green: A Short Review," *Journal of Medicine*, vol. 24, No. 1, pp. 10-27, 1993.

(Continued)

*Primary Examiner*—D L Jones
(74) *Attorney, Agent, or Firm*—The Web Law Firm

(57) ABSTRACT

This invention relates to an in-vivo diagnostic method based on near infrared radiation (NIR radiation) that uses water-soluble dyes and their biomolecule adducts, each having specific photophysical and pharmaco-chemical properties, as a contrast medium for fluorescence and transillumination diagnostics in the NIR range, to new dyes and pharmaceuticals containing such dyes.

3 Claims, 1 Drawing Sheet

OTHER PUBLICATIONS

Boyer et al., "Evaluation of Near Infrared Dyes as Labels for Immunoassays Utilizing Laser Diode Detection: Development of Near Infrared Dye Immunoassay (NIRDIA)," *Analytical Letters*, vol. 25, No. 3, pp. 415-428, 1992.

Lansdorp et al., "Single Laser Three Color Immunofluorescence Staining Procedures Based on Energy Transfer Between Phycoerythrin and Cyanine 5," *Cytometry*, vol. 12, pp. 723-730, 1991.

Alveryd et al., "Lightscanning Versus Mammography for the Detection of Breast Cancer in Screening and Clinical Practice," *Cancer*, vol. 65, No. 8 pp. 1671-1677, 1990.

Ernst et al., "Cyanine Dye Labeling Reagents for Sulfhydryl Groups," *Cytometry*, vol. 10, pp. 3-10, 1989.

Satori et al., "Laser-Induced Autofluorescence of Human Arteries," *Circulation Research*, vol. 63, No. 6, pp. 1053-1059, 1988.

Navarro et al., "Contrast in diaphanography of the breast," *Am. Assoc. Phys. Med.*, vol. 15, No. 2, pp. 181-187, 1988.

Beuthan et al., "IR-Diaphanoscopy in Medicine" *Medical Optical Tomography: Functional Imaging and Monitoring*, vol. ISII, pp. 263-282, 1993.

Slominskii et al., "Tricarbocyanines with Hydrocarbon Rings in the Chromophore" *Ukrainskii Khimicheskii Zhurnal*, vol. 40, No. 6, pp. 61-64, 1974.

Kuramoto, "The role of excited singlet molecular oxygen in the photodegradation of functional squarylium dyes," *JSDC*, vol. 106, pp. 181-186, 1990.

Kuramoto et al., "Synthesis and Characterization of Deep-Coloured Squarylium Dyes for Laser Optical Recording Media," *Dyes and Pigments*, vol. 11, pp. 21-35, 1989.

\* cited by examiner

NEAR INFRARED IMAGING AGENT

CROSS REFERENCE TO RELATED APPLICATIONS

This application is a continuation of U.S. patent application Ser. No. 11/093,082, filed Mar. 29, 2005, now abandoned; which is a divisional of U.S. patent application Ser. No. 10/368,997, now U.S. Pat. No. 6,913,743 filed Feb. 19, 2003; which is a continuation of U.S. patent application Ser. No. 10/180,272, filed Jun. 26, 2002, now U.S. Pat. No. 6,926,885; which is a continuation of U.S. patent application Ser. No. 09/850,660, filed May 7, 2001, now U.S. Pat. No. 7,025,949; which is a divisional of U.S. patent application Ser. No. 09/518,947, filed Mar. 6, 2000, now U.S. Pat. No. 6,258,340, which is a continuation of U.S. patent application Ser. No. 08/849,369, filed Nov. 7, 1997, now U.S. Pat. No. 6,083,485.

BACKGROUND OF THE INVENTION

1. Field of the Invention

This invention relates to an in-vivo diagnostic method based on near infrared radiation (NIR radiation) that uses water-soluble dyes and their biomolecule adducts, each having specific photophysical and pharmaco-chemical properties, as a contrast medium for fluorescence and transillumination diagnostics in the NIR range, to new dyes and pharmaceuticals containing such dyes.

2. Description of Related Art

Diagnosability of diseases is very much dependent on obtaining information about the structures, as well as changes, of tissues of the profound layers that are not primarily accessible. In addition to palpating, exposing or puncturing these tissues, such information can be gained using sophisticated imaging methods such as x-raying, magnetic resonance tomography, or ultrasonic diagnosis.

As biological tissue shows a relatively high permeability for long wave light in the range of 650-1000 nm, a diagnostician can therefore use a completely different method of tissue imaging. The fact that light in the near infrared range can permeate through several centimeters of tissue is utilized in transillumination imaging. This technique as yet facilitates diagnosis of inflammations of the paranasal and maxillary sinuses as well as the detection of accumulated fluids or blood in superficial zones of tissue (Beuthan, J., Müller, G.; Infrarotdiaphanoskopie, *Med. Tech.* 1 (1992) 13-17).

Attempts at detecting breast tumours have been unsatisfactory so far (Navarro, G. A.; Profio, A. E.; Contrast in diaphanography of the breast; *Med. Phys.* 150 (1988) 181-187; Aspegren, K.; Light Scanning Versus Mammography for the Detection of Breast Cancer in Screening and Clinical Practice, *Cancer* 65 (1990) 1671-77) but there may be better results in the future due to most recent engineering progress (Klingenbeck, J.; Laser-Mammography with NIR-Light, *Gynäkol.-Geburtsch.-Randsch.* 33 Suppl.1 (1993) 299-300); Benaron, D. A.; Optical Imaging reborn with technical advances, *Diagnostic Imaging* (1994) 69-76).

In addition to detecting non-absorbed radiation, fluorescence radiation emitted after near infrared light treatment can provide tissue-specific information. This so-called autofluorescence is used to distinguish atherosclerotic and normal tissue (Henry, P. D. et al., Laser-Induced Autofluorescence of Human Arteries, Circ. Res. 63 (1988) 1053-59).

The main problem of applying near infrared radiation is the extraordinarily wide scattering of the light which permits only a rather blurred image of a clearly contoured object despite different photophysical properties. The problem increases the greater the distance from the surface is and may be considered the major limiting factor of both transillumination and detection of fluorescence radiation.

Suitable fluorescent dyes that accumulate in diseased tissue (above all, in tumours) and that show a specific absorption and emission behaviour, may contribute towards enhancing the distinction of healthy from diseased tissue. The change caused by absorbing irradiated (scattered) light, or fluorescence induced by exciting radiation, is detected and provides the actual tissue-specific information.

Examples of using dyes for in-vivo diagnostics in humans are photometric methods of tracing in the blood to determine distribution areas, blood flow, or metabolic and excretory functions, and to visualize transparent structures of the eye (ophthalmology). Preferred dyes for such applications are indocyanine green and fluorescein (Googe, J. M. et al., Intraoperative Fluorescein Angiography; *Ophthalmology,* 100 (1993), 1167-70).

Indocyanine green (Cardiogreen) is used for measuring the liver function, cardiac output and stroke volume, as well as the blood flow through organs and peripheral blood flows (*I. Med.* 24 (1993) 10-27); in addition, they are being tested as contrast media for tumour detection. Indocyanine green binds up to 100% to albumin and is mobilized in the liver. Fluorescent quantum efficiency is low in a hydrous environment. Its $LD_{50}$ (0.84 mmol/kg) is great enough; strong anaphylactic responses may occur. Indocyanine green is unstable when dissolved and cannot be applied in saline media because precipitation will occur.

Photosensitizers designed for use in photodynamic therapy (PDT) (including haematoporphyrin derivatives, photophrin II, benzoporphyrins, tetraphenyl porphyrins, chlorines, phthalocyanines) were used up to now for localizing and visualizing tumours (Bonnet, R.; New photosensitizers for the photodynamic therapy of tumours, *SPIE* Vol. 2078 (1994)). It is a common disadvantage of the compounds listed that their absorption in the wavelength range of 650-1200 nm is only moderate. The phototoxicity required for PDT is disturbing for purely diagnostic purposes. Other patent specifications dealing with these topics are: U.S. Pat. No. 4,945,239; WO 84/04665, WO 90/10219, DE 4136769, DE 2910760.

U.S. Pat. No. 4,945,239 describes a great number of equipment arrangements for detecting breast cancer using transillumination and mentions the known fluorescein, fluorescamin, and riboflavin as contrast-improving absorption dyes. These dyes share the disadvantage that they absorb in the visible wavelength range of 400-600 nm in which light transmission capacity of tissue is very low.

DE 4136769 describes an apparatus for detecting fluorescence of tissue areas enriched with fluorescent substances. These substances are bacterial chlorophyll and its derivatives, and naphthalocyanines. These structures show absorptions in the range of 700-800 nm at absorbency indices of up to 70000 1 $mol^{-1}$ $cm^{-1}$. In addition to their fluorescent properties, the compounds mentioned here are capable of generating singlet oxygen by radiation, thus having a cytotoxic effect (photosensitizers for photodynamic therapy). This photosensitizing activity is highly undesirable for a pure, inactive diagnostic agent.

Furthermore, synthesis of bacterial chlorophyll compounds is expensive and requires much effort as natural products have to be used as parent substances; the naphthalocyanines, however, frequently show a very low photostability. The known compounds of these classes are hardly soluble in water, and synthesizing uniform hydrophilic derivatives is costly.

WO 84/04665 describes an in-vivo method for the fluorescence detection of tumours using the following photosensitizers: haematoporphyrin and its derivative (Hp and HpD), uro- and copro- and protoporphyrin as well as numerous mesosubstituted porphyrins, and dyes such as riboflavin, fluorescein, acridine orange, berberine sulfate and tetracyclines. The photophysical and pharmacochemical requirements mentioned above are not met by said substances.

Folli et al., *Cancer Research* 54, 2643-2649 (1994), describe a monoclonal antibody connected with a cyanine dye that was used for detecting a tumour implanted subcutaneously. Detection of profounder pathologic processes, however, requires much improved dyes. Higher dye dosages render the use of antibodies as carriers unsuitable in view of the side effects to be expected.

Cyanine dyes and polymethine dyes related to them are also used as photographic layers. Such dyes need not have any luminescent properties. Cyanine dyes that have luminescent (fluorescent) properties have been synthesized for use in fluorescent microscopy and flow cytometry and coupled with biomolecules such as compounds containing iodine acetyl groups as specific labeling reagents for sulfhydryl groups of proteins (Waggoner, A. S. et al., Cyanine dye Labeling Reagents for Sulfhydryl Groups, *Cytometry*, 10, (1989), 3-10). Proteins are labeled and isolated in this way. More references: *Cytometry* 12 (1990) 723-30; *Anal. Lett.* 25 (1992) 415-28; *Bioconjugate Chem.* 4 (1993) 105-11.

DE 39 12 046 by Waggoner, A. S. describes a method for labeling biomolecules using cyanine and related dyes such as merocyanine and styryls that contain at least one sulfonate or sulfonic acid grouping. This specification relates to a single and two-step labeling method in a hydrous environment, with a covalent reaction taking place between the dye and the amine, hydroxyl, aldehyde or sulfhydryl group on proteins or other biomolecules.

DE 3828360 relates to a method for labeling antitumour antibodies, in particular, antibodies specific to melanoma and colonic cancer, using fluorescein and indocyanine green for ophthalmologic purposes. Bonding of indocyanine green to biomolecules is not covalent (dye-antibody combination, mixture).

The known, state-of-the-art methods of in-vivo diagnosis using NIR radiation thus show a number of disadvantages that prevented their wide application in medical diagnostics.

Direct use of visible light or NIR radiation is restricted to superficial body zones, which is due to the widely scattered incident light.

Adding dyes to improve contrast and resolution, however, gives rise to a number of other problems. The dyes should meet the requirements that generally apply to diagnostic pharmaceuticals. As these substances are mostly applied at higher doses and for a longer diagnostic period, they should be low-toxic. In addition, dyes suitable for diagnostic purposes should be well soluble in water and sufficiently stable in chemical and photophysical respect, at least for as long as the diagnostic period lasts. Stability as regards metabolization in the system is also desirable.

So far, neither dyes nor a suitable method for in-vivo diagnosis using NIR radiation has been available.

It is therefore an object of this invention to provide a method of in-vivo diagnosis that overcomes the disadvantages of prior art.

SUMMARY OF THE INVENTION

Figure 1:
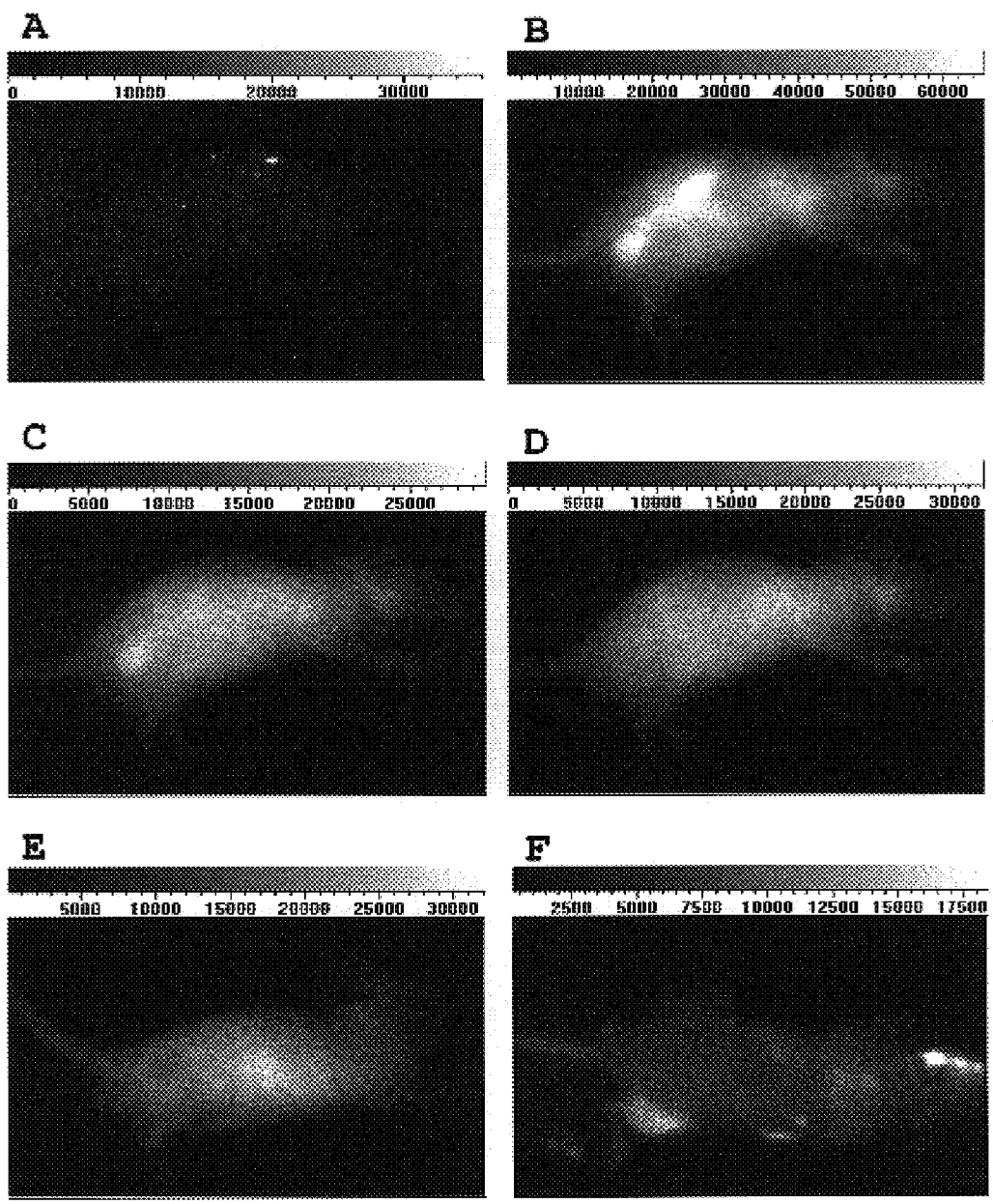
FIG. 1 shows fluorescent light images (black-and-white) of a mouse (Swiss Nude) at various points in time after i.v. application of 3.8 mmol/kg body weight of 2-[7-[1,3-dihydro-3,3-dimethyl-5-(methoxycarbonyl)-1-(4-sulfobutyl)-2H-indol-2-yliden]-1,3,5-heptatrienyl]-3,3-dimethyl-5-(methoxycarbonyl)-1-(4-sulfobutyl)-3H-indolium, sodium salt. Photographs A-E are right lateral images, and photograph F is a posterior image, taken at the following times:
A: prior to application,
B: 30 seconds after application,
C: 1 minute after application,
D: 10 minutes after application,
E: 1 hour after application, and
F: 18 hours after application.

This problem is solved according to the invention by providing a method of in-vivo diagnosis using NIR radiation in which compounds of the general formula I

$$B_l\text{—}(F\text{—}W_n)_m \qquad (I)$$

are used,
wherein
l represents a number from 0 to 6, n a number from 0 to 10, and m a number from 1 to 100,
B is a biological detecting unit having a molecular weight of up to 30000 that bonds to specific cell populations or selectively to receptors, or accumulates in tissues or tumours, or generally stays in the blood, or is a macromolecule that bonds non-selectively;
F represents a dye showing maximum absorption in the range of 650 to 1200 nm;
W represents a hydrophilic group that improves water-solubility, with the n-octanol-water distribution coefficient of the compound according to formula I being less than or equal to 2.0 for l=0;

as well as their physiologically tolerable salts.

DETAILED DESCRIPTION OF THE INVENTION

The present invention includes compounds of the general formula I

$$B_l\text{—}(F\text{—}W_n)_m \qquad (I)$$

are used,
wherein
the letter l represents a number from 0 to 6, n represents a number from 0 to 10, and m represents a number from 1 to 100,
B is a biological detecting unit having a molecular weight of up to 30,000 that bonds to specific cell populations or selectively to receptors, or accumulates in tissues or tumours, or generally stays in the blood, or is a macromolecule that bonds non-selectively;
F represents a dye showing maximum absorption in the range of 650 to 1200 nm; and
W represents a hydrophilic group that improves water-solubility, with the n-octanol-water distribution coefficient of the compound according to formula I being less than or equal to 2.0 for L=0;

as well as their physiologically tolerable salts.

Compounds of the general formula I that are particularly well-suited for the method according to the invention are those in which, for example, B is an amino acid, a peptide, CDR (complementarity determining region), an antigen, a hapten, an enzyme substrate, an enzyme cofactor, biotin, a carotinoid, a hormone, a neurohormone, a neurotransmitter, a growth factor, a lymphokin, a lectin, a toxin, a carbohydrate, an oligosaccharide, a polysaccharide, a dextrane, an oligonucleotide or a receptor-bonding pharmaceutical.

Furthermore, such compounds of the general formula I are particularly appropriate for the method according to the invention in which, for example, F
represents a cyanine dye of the general formula IIa

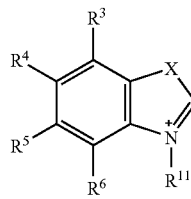 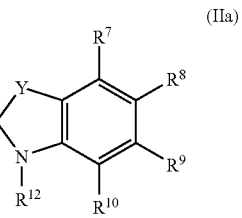

(IIa)

wherein
r represents the numbers 0, 1 or 2, on condition that, for r=2, the respective fragments $L^6$ and $L^7$ that occur in duplicate may be the same or different,
$L^1$ to $L^7$ are same or different, each independently representing a fragment CH or CR, where
R is a halogen atom, a hydroxy, carboxy acetoxy, amino, nitro, cyano or sulfonic acid group or an alkyl, alkenyl, hydroxyalkyl, carboxyalkyl, alkoxy, alkoxycarbonyl, sulfoalkyl, alkylamino, dialkylamino or halogenalkyl residue containing up to 6 carbon atoms, an aryl, alkylaryl, hydroxyaryl, carboxyaryl, sulfoaryl, arylamino, diarylamino, nitroaryl or halogenaryl residue containing up to 9 carbon atoms, or where R represents a bond that bonds to another residue R and forms a 4- to 6-member ring together with the interspersed residues $L^1$ to $L^7$, or where R represents one bond, respectively, at two different positions that are linked via a —CO— fragment,
$R^3$ to $R^{12}$ are same or different, each independently representing a hydrogen atom, a residue B or W as defined above, or an alkyl or alkenyl residue containing up to 6 carbon atoms or an aryl or aralkyl residue containing up to 9 carbon atoms, said alkyl, alkenyl, or aryl or aralkyl residue optionally carrying an additional residue W as defined above, or to each pair of adjacent residues $R^3$ to $R^{10}$ are annealed 5- to 6-member rings that may be saturated, unsaturated or aromatic, and that may optionally carry an additional residue R as defined above, with due regard for the interspersed C atoms, X and Y are same or different, each independently representing an O, S, Se or Te or a —C(CH$_3$)$_2$—, —CH═CH— or —CR$^{13}$R$^{14}$-fragment,
where $R^{13}$ and $R^{14}$ independently represent a hydrogen atom, a residue B or W as defined above, or an alkyl or alkenyl residue containing up to 6 carbon atoms or an aryl or aralkyl residue containing up to 9 carbon atoms, the alkyl, alkenyl, aryl or aralkyl residue optionally carrying an additional residue W as defined above,
represents a squarain dye of the general formula II b

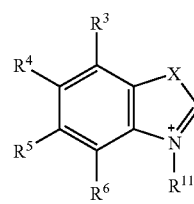 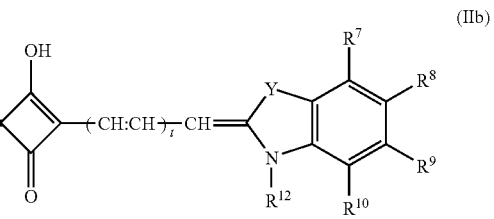

(IIb)

wherein
s and t independently represent the numbers 0 or 1 on the condition that s and t do not represent the number 1 at the same time,
and $R^3$ to $R^{12}$, x and y are as defined above,
represents a styryl dye of the general formula II c

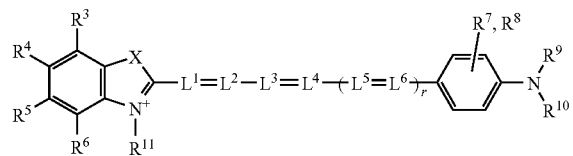

(IIc)

wherein
r, $L^1$ to $L^6$, $R^3$ to $R^{11}$ and X are as defined above,
or represents a merocyanine dye of the general formula II d

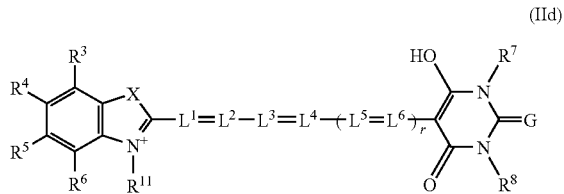

(IId)

wherein r, $L^1$ to $L^6$, $R^3$ to $R^8$, $R^{11}$ and X are as defined above and G represents an oxygen or sulfur atom.

Such compounds of the general formula I are particularly appropriate for the method according to the invention in which, for example, W is a carboxy or sulfonic acid group or a carboxyalkyl group or an alkoxycarbonyl group or an alkoxyoxoalkyl group containing up to 12 carbon atoms, represents a residue of the general formulas III

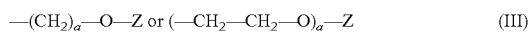

$$-(CH_2)_a-O-Z \text{ or } (-CH_2-CH_2-O)_a-Z \quad (III)$$

wherein a represents the numbers 0 to 6

Z comprises a hydrogen atom or an alkyl residue containing 3 to 6 C atoms that includes 2 to n-1 hydroxy groups, with n being the number of C atoms, or an aryl or aralkyl residue containing 6 to 10 C atoms and carrying 2 to 4 additional hydroxy groups, or an alkyl residue containing 1 to 6 C atoms and carrying 1 to 3 additional carboxy groups, or an aryl residue containing 6 to 9 C atoms and carrying 1 to 3 additional carboxyl groups, or an aralkyl residue or a nitroaryl or a nitroaralkyl residue containing 6 to 15 C atoms, or a sulfoalkyl residue containing 2 to 4 C atoms carrying 1 to 3 additional carboxy groups, or represents a residue of the general formulas III a or III b

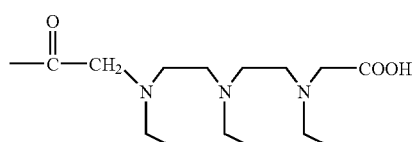

(IIIa)

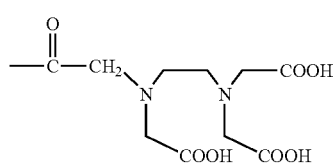

(IIIb)

or a residue of the general formula IIIc $$-(CH_2)_o-(CO)_p-NR^1-(CH_2)-(NH-CO)_q-R^2 \quad (IIIc)$$

wherein o and s independently represent the numbers 0, 1, 2, 3, 4, 5 or 6, p and q independently represent 0 or 1, $R^1$ and $R^2$ independently represent a residue Z as defined above except the substituents of the general formulas IIIa and IIIb, or independently represent a residue of the general formulas IIId or IIIe

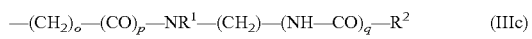

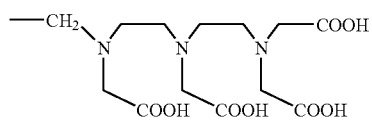

(IIId)

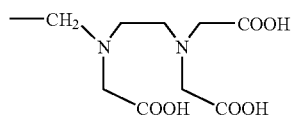

(IIIe)

on the condition that p and q=1, or represents a residue of the general formula IIIc as defined above.

The compounds used for the method according to the invention are characterized in that they absorb and fluoresce in the wavelength range of 650 to 1200 nm, have absorption coefficients of approx. 100 000 100,000 1 $mol^{-1}$ $cm^{-1}$ and more and, where fluorescence is desirable, have a fluorescence quantum efficiency greater than 5%, are sufficiently water-soluble, tolerable and stable in vitro and in vivo as well as photostable. They are discharged as completely as possible in as short a time as possible. The compounds used according to the invention are synthesized easily and at a favorable price in only a few reaction steps from parent materials that are available on the market.

When applying the method according to the invention in in-vivo diagnosis, one or several substances of the general formula I is/are administered to the tissues, for example, by intravenous injection, then they are irradiated with light from the visible to the near infrared range of 650 to 1200 nm. Radiation that is not absorbed and fluorescence radiation are recorded separately or simultaneously, or against each other with a delay. A synthetic image is generated from the data obtained.

Fluorescent images can be recorded using various methods. Preferred are those methods where the tissue is irradiated extensively, fluorescence information is visualized in local resolution by a CCD camera, or where the tissue sectors to be imaged are scanned by a light ray concentrated in a fibre optical waveguide and signals obtained are converted into an image by computing. The light is beamed in in the narrow-band range at wavelengths close to the maximum absorption or at fluorescence-exciting wavelengths of the compounds of the invention. Radiation that was not absorbed can be recorded as described, and signals obtained be processed.

The irradiation angle and the angle of observation can be selected from case to case to meet anatomic and optimum contrast requirements. The sensitivity of the method may be improved by subtracting the images prior to and after administering the dye. Evaluating the time curve of dye-related changes may reveal useful additional information for the diagnosis.

The measurement methods used are known to a person skilled in the art. The expert will also know what equipment parameters should be set to obtain optimum recording and evaluation conditions at given absorption or fluorescence wavelengths of the dyes of the general formula I used according to the invention.

The compounds of the general formula I used for the method of the invention cover a wide range of exciting and emission wavelengths due to the variable structure of the dye system F. It is possible to gain products with exciting wavelengths that correspond to a specific source of excitation, e.g. at the diode laser unit, and are therefore adapted to a given measuring system or equipment component.

The techniques described even permit localization of small objects having a volume of only a few $mm^3$ at the profounder layers of tissue or in non-transparent body fluids. Due to light scattering and the limited resolution it entails it is still difficult to determine the exact shape and size of such objects but this is not required to solve some important diagnostic questions.

Surprisingly, a fluoroscopic image of a mouse (Swiss Nude) taken after applying a cyanine dye using a CCD camera showed a 1000 times greater fluorescent intensity as compared to a similarly dosed porphyrin.

The method described that uses the compounds of the invention is particularly suitable for the visualization of tissue without pathological alterations, systemic diseases, tumours, blood vessels, atherosclerotic plaques, perfusion and diffusion.

The compounds used according to the invention are applied to the tissue in different ways. Intravenous administration of the dyes is particularly preferred.

Dosage may be quite different depending on the purpose of application. The goal to be achieved is a detectable concentration of dye in the tissue zone to be diagnosed, for which a concentration of 1-100 µg/ml in the tissue or in body fluids will mostly be sufficient. This concentration is reached by direct injection into small body cavities or small blood or lymph vessels, normally by applying 0.1-100 mg of the respective dye contained in 0.1 to 10 ml of vehicle liquid. In this case, 1 to 10 mg of dye are preferred. Higher doses are mostly required to stain blood vessels or to detect specific tissues or structures after intravenous injection (greater than or equal to 100 mg). The upper limit of dosage is only set by the tolerability of the respective substances and preparations.

Thus, the invention relates to the use of compounds of the type $B_l-(F-W_n)_m$, in which F represents a dye from the class of polymethine dyes, in particular, cyanine dyes. Merocyanine, styryl, oxonol and squarilium dyes may also be used. W is a structural element that contributes essentially to the hydrophilia of the whole molecule. Particularly preferred are compounds in which l represents the number 0, with their n-octanol/water distribution coefficient being smaller than 2 (n-octanol/0.01 M TRIS buffer containing 0.9% of sodium chloride, set to pH 7.4, both phases saturated against each other).

A biological detecting unit B may, for example, be an amino acid, a peptide, a CDR (complementarity determining regions), an antigen, a hapten, an enzyme substrate, an enzyme cofactor, biotin, a carbotinoid, a hormone, neurohormone, neurotransmitter, a growth factor, a lymphokin, a lectin, a toxin, a carbohydrate, an oligosaccharide, a polysaccharide, a dextran, an oligonucleotide made resistant to nucleases or a receptor-bonding pharmaceutical.

Compounds from the above-mentioned groups include, for example, oxytocins, vasopressins, angiotensins, melanocyte-stimulating hormones, somatostatins, tyrotropin-releasing hormones, gonadotropin-releasing hormones, testosterones, estradiols, progesterones, cortisols, aldosterones, vitamin D, gastrins, secretins, somatropins, insulins, glucagons, calcitonin, STH-releasing hormones, prolactins, encephalins, dopamines, noradrenalines, serotonins, epinephrines, interleukines, angiogenins, thymopoietins, erythropoietins, fibrinogens, angiotensinogens, mecamylamines, ranitidine, cimetidine, lovastatines, isoproterenol derivatives or transferrin.

These substances facilitate accumulation in specific parts of the body by targeting the biological detecting unit through certain mechanisms. These mechanisms include bonding to extracellular structures, accumulation through various biological transport systems, recognition of cell surfaces or recognition of intracellular components.

Other compounds can be used according to the invention in which B is a non-selectively bonding macromolecule, such as polylysine, polyethylene glycol, methoxypolyethylene glycol, polyvinyl alcohol, dextran, carboxydextran or a cascade polymer-like structure that is covalently bonded to F.

The alkyl-, aryl- or aralkyl residue with hydroxy groups contained in the compounds of the general formula I used according to the invention, are for example, 2-hydroxyethyl-, 2-hydroxypropyl-, 3-hydroxypropyl-, 4-hydroxybutyl-, 2,3-dihydroxypropyl-, 1,3-dihydroxyprop-2-yl-, tris-(hydroxymethyl)-methyl-, 1,3,4-trihydroxybut-2-yl-glucosyl-, 4-(1,2-dihydroxyethyl)phenyl- or 2,4-, 2,5-, 3,5- or 3,4-dihydroxyphenyl residues.

An alkyl-, aryl- or aralkyl residue containing 1 to 3 carboxy groups may be, for example, a carboxymethyl-, carboxyethyl-, carboxypropyl-, carboxybutyl-, 1,2-dicarboxyethyl-, 1,3-dicarboxypropyl-, 3,5-dicarboxyphenyl-, 3,4-dicarboxyphenyl-, 2,4-dicarboxyphenyl or 4-(1,2-dicarboxyethyl)-phenyl residue.

A sulfoalkyl residue preferably is a 2-sulfoethyl-, 3-sulfopropyl- and 4-sulfobutyl residue.

Especially preferred are compounds in which W takes the position of $R^4$ and/or $R^8$, $R^6$ and/or $R^{10}$, as well as $R^{11}$ and/or $R^{12}$. Equally preferred are compounds in which W takes the position $R^3$ and $R^5$ and/or the position $R^7$ and $R^9$.

The dyes used according to the present invention absorb in the spectral range from 650 nm to 1200 nm. The absorption coefficients of the compounds are ca. 100,000 1 mol$^{-1}$ cm$^{-1}$ and more for one dye molecule. Fluorescent quantum efficiencies are greater than 5% for all dyes used for fluorescent imaging.

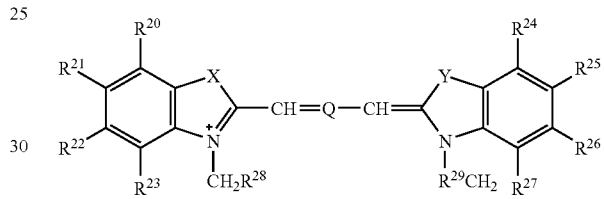

(V)

Another object of this invention are cyanine dyes of the general formula V.

where

Q represents a fragment

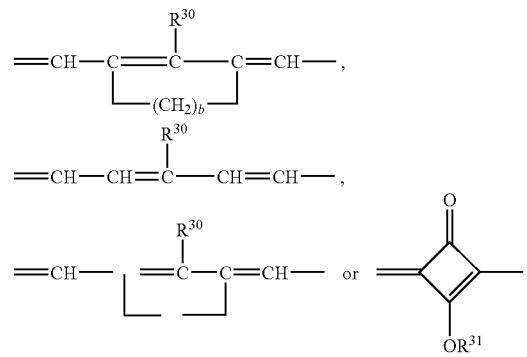

where $R^{30}$ represents a hydrogen atom, a hydroxy group, a carboxy group, an alkoxy residue containing 1 to 4 carbon atoms or a chlorine atom, b is an integer (2 or 3), $R^{31}$ represents a hydrogen atom or an alkyl residue containing 1 to 4 carbon atoms, X and Y independently represent an —O—, —S—, —CH=CH— or —C(CH$_2$R$^{32}$)(CH$_2$R$^{33}$)— fragment each, $R^{20}$ to $R^{29}$, $R^{32}$ and $R^{33}$ independently represent a hydrogen atom, a hydroxy group, a carboxy group, a sulfonic acid residue or a carboxyalkyl-, alkoxycarbonyl or alkoxyoxoalkyl residue containing up to 10 C atoms or a sulfoalkyl residue containing up to 4 C atoms, or a non-selectively bonding macromolecule or a residue of the general formula VI

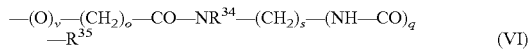

$$—(O)_v—(CH_2)_o—CO—NR^{34}—(CH_2)_s—(NH—CO)_q—R^{35} \quad (VI)$$

on the condition that, where X and Y are O, S, —CH=CH— or —C(CH$_3$)$_2$—, at least one of the residues R$^{20}$ to R$^{29}$ corresponds to a non-selectively bonding macromolecule or a compound of the general formula VI,
where
o and s equal 0 or independently represent an integer between 1 and 6,
q and v independently represent 0 or 1,
R$^{34}$ represents a hydrogen atom or a methyl residue,
R$^{35}$ represents an alkyl residue containing 3 to 6 C atoms and comprising 2 to n-1 hydroxy groups, with n being the number of C atoms, or an alkyl residue containing 1 to 6 C atoms that carries 1 to 3 additional carboxy groups, an aryl residue containing 6 to 9 C atoms or arylalkyl residue containing 7 to 15 C atoms, or a residue of the general formula IIId or IIIe

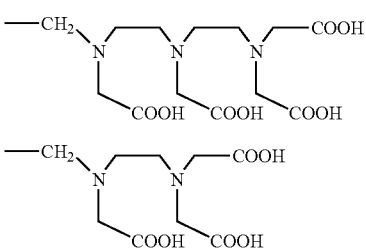

on the condition that q is 1,
or a non-selectively bonding macromolecule,
R$^{20}$ and R$^{21}$, R$^{21}$ and R$^{22}$, R$^{22}$ and R$^{23}$, R$^{24}$ and R$^{25}$, R$^{25}$ and R$^{26}$, R$^{26}$ and R$^{27}$, together with the interspersed carbon atoms, form a 5- or 6-member aromatic or saturated annealed ring,
as well as their physiologically tolerable salts.

In the compounds according to the invention of the general formula V, the alkyl-, aryl- or aralkyl residues containing hydroxy- or carboxy groups have the preferred composition as defined above.

The following are particularly preferred cyanine dyes:

5-[2-[(1,2-dicarboxyethyl)amino]-2-oxoethyl]-2-[7-[5-[2-[(1,2-dicarboxyethyl)amino]-2-oxoethyl]-1,3-dihydro-3,3-dimethyl-1-(4-sulfobutyl)-2H-indol-2-yliden]-1,3,5-heptatrienyl]-3,3-dimethyl-1-(4-sulfobutyl)-3H-indolium, inner salt, potassium hydrogen salt;

2-[7-[5-[2-[(11-carboxy-2-oxo-1,4,7,10-tetraaza-4,7,10-tri(carboxymethyl)-1-undecyl)amino]-2-oxoethyl]-1,3-dihydro-3,3-dimethyl-1-ethyl-2H-indol-2-yliden]-1,3,5-heptatrienyl]-3,3-dimethyl-1-(4-sulfobutyl)-3H-indolium, inner salt;

2-[7-[1,3-dihydro-3,3-dimethyl-5-[2-[(methoxypolyoxyethylene)-amino]-2-oxoethyl]-1-(4-sulfobutyl)-2H-indol-2-yliden]-1,3,5-heptatrienyl]-3,3-dimethyl-5-[2-[(methoxypolyoxyethylene)amino]-2-oxoethyl]-1-(4-sulfobutyl)-3H-indolium, sodium salt;

2-[7-[1,3-dihydro-3,3-dimethyl-1-(4-sulfobutyl)-2H-indol-2-yliden]-1,3,5-heptatrienyl]-3,3-dimethyl-5-(methoxypolyoxyethylene)aminocarbonyl-1-(4-sulfobutyl)-3H-indolium, sodium salt;

3-(3-carboxypropyl)-2-[7-[3-(3-carboxypropyl)-1,3-dihydro-3-methyl-1-(4-sulfobutyl)-2H-indol-2-yliden]-1,3,5-heptatrienyl]-3-methyl-1-(4-sulfobutyl)-3H-indolium, sodium salt;

2-[[3-[[3-(3-carboxypropyl)-1,3-dihydro-3-methyl-1-(4-sulfobutyl)2H-indol-2-yliden]methyl]-2-hydroxy-4-oxo-2-cyclobuten-1-yliden]methyl]-1,1-dimethyl-3-ethyl-1H-benz(e)indolium, inner salt;

2-[7-[1,3-dihydro-5-[2-[(2,3-dihydroxypropyl)amino]-2-oxoethyl]-3,3-dimethyl-1-(4-sulfobutyl)-2H-indol-2-yliden]-1,3,5-heptatrienyl]-5-[2-[(2,3-dihydroxypropyl)amino]-2-oxoethyl]-3,3-dimethyl-1-(4-sulfobutyl)-3H-indolium, sodium salt.

Another important characteristic of the compounds of the invention and the compounds used according to the invention is their hydrophilia marked by an n-octanol/water distribution coefficient smaller than 2.0 (distribution coefficient n-octanol/0.01 M TRIS buffer containing 0.9% sodium chloride, set to pH 7.4, both phases saturated against each other). The compounds do not have any distinct photosensitizing or phototoxic properties that would be undesirable in a diagnostic reagent. They are tolerated well, and discharged.

The hydrophilic behaviour of the compounds of the invention make them differ from dyes that have been proposed for use in in-vivo diagnostics. Especially with cyanine dyes, fluorescent quantum efficiency values, due to aggregation, drop dramatically in a hydrous environment, and are comparable to values measured in non-polar solvents; increased solubility in water and the space requirements of the hydrophilic groups suppress the formation of aggregates and micelles.

A group of preferred compounds shows little protein affinity; its pharmacokinetic behaviour is similar to that of insulin or saccharose, for example.

Surprisingly, these compounds showed diagnostically sufficient accumulation in specific structures of the system, e.g. in tumours, despite their simple molecular structure. When the dye has spread equally throughout the organism, its elimination, compared to the surrounding tissue, is delayed in tumour zones.

Tolerance of the substances is very good. Substances having LD$_{50}$ values greater than 0.5 mmol/kg body weight referred to a single dye molecule, are particularly preferred.

The compounds of the invention and the compounds used according to the invention are characterized by great in-vitro and in-vivo stability, as well as photostability. When the aqueous solution is allowed to stand in a daylit room, 98% of each of the compounds that are particularly preferred show no changes after 2 days, 70% show no changes after 12 days.

The photophysical and pharmacokinetic properties described of the compounds of the invention and the compounds used according to the invention, also differ from those of the only cyanine dye approved for application in humans: indocyanine green (Cardiogreen).

Another object of the present invention are compounds of the general formula I in which the l-values of B are greater than or equal to 1, preferably 1 or 2.

Cyanine dyes can be synthesized that have a great extinction coefficient when absorbing light at wavelengths from 650 to 120 nm, and that fluoresce with great efficiency. Cyanine dyes of the invention and cyanine dyes used according to the invention are mainly synthesized according to methods known from the literature, for example F. M. Hamer in *The Cyanine Dyes and Related Compounds*, John Wiley and Sons, New York, 1964; *Cytometry* 10 (1989) 3-10; 11 (1990) 418-430; 12 (1990) 723-730; *Bioconjugate Chem.* 4 (1993) 105-11, *Anal. Biochem.* 217 (1994) 197-204; *Tetrahedron* 45 (1989) 4845-66, European Patent No. EP 0 591 820 A1.

The dye-biomolecule adducts of the general formula I used according to the invention are prepared by reacting a known compound F—$W_n$ prepared according to the methods mentioned above with a biological detecting unit B.

The compound F—$W_n$ should therefore contain at least one, preferably exactly one, grouping that can react covalently to an amine, hydroxy, aldehyde or sulfhydryl group on the biological detecting units. Such groupings are known from the literature and described in some detail, for example, in DE 39 12 046.

Particularly preferred are isothiocyanate, isocyanate, and hydroxysuccinimide ester or hydroxysulfosuccinimide ester groupings that are reactive to amino functions and form a thiourea, urea and amide bridge, as well as halogenacetyl and succinimide groupings that are reactive to sulfhydryl groups and form a thioester bridge.

Furthermore, carboxy groups with alcoholic functions may form ester linkages or ether structures using appropriate activating reagents (e.g. DCC), and aldehyde functions combined with hydrazines may result in imine structures.

The reactive groupings mentioned are added to the dyes of the invention or dyes used according to the invention of the general formula I or their synthetic predecessors, or existing function groups are converted into the reactive groupings. The reactive groupings may be directly bonded to the dye system via so-called linker structures (e.g. alkyl chains, aralkyl structures).

The F—$W_n$ compounds are preferably reacted with the biological detecting units B in DMF or a hydrous environment or DMF/water mixtures at pH values between 7.4 and 10. The molar proportion of dye and biomolecule (charging ratio) is determined using absorption spectrometry. Components that are not bound are separated by chromatography or filtering.

Macromolecules that have the appropriate function groups may be coupled to the dyes in a similar way.

The substances may have quite different properties. Their molecular weight may be from a few hundreds to more than 100,000. The substances can be neutral or electrically charged. Salts of acid dyes and physiologically acceptable bases, such as sodium, methyl glutamine, lysine, or salts containing lithium, calcium, magnesium, gadolinium in the form of cations.

The dye-biomolecule adducts thus gained excellently meet the above photophysical, toxicological, chemical and economic requirements.

Another object of the present invention is the use of cyanine dyes of the general formula V for in-vivo diagnosis using NIR radiation, in analogy to the use of compounds of the general formula I.

Yet another object of the present invention are diagnostic reagents that contain compounds of the general formulas V or I.

These reagents are produced according to methods known to persons skilled in the art, optionally by adding common adjuvants, diluents and the like. This includes physiologically tolerable electrolytes, buffers, detergents and substances for adjusting osmolarity and for improving stability and solubility such as cyclodextrine. Sterility of the preparations during their production and, in particular, before their application is to be ensured by taking the steps common in pharmaceutics.

The invention will now be explained by the following examples.

EXAMPLES

Example 1

Preparation of 5-[2-[[(1,2-dicarboxyethyl)amino]-2-oxoethyl]-2-[7-[5-[2-(1,2-dicarboxyethyl)amino]-2-oxoethyl]-1,3-dihydro-3,3-dimethyl-1-(4-sulfobutyl)-2H-indol-2-yliden]-1,3,5-heptatrienyl]-3,3-dimethyl-1-(4-sulfobutyl)-3H-indolium, inner salt, potassium hydrogen salt.

Di-N-hydroxysuccinimide ester is prepared from 5-carboxymethyl-2-[7-[5-carboxymethyl-1,3-dihydro-3,3-dimethyl-1-(4-sulfobutyl)-2H-indol-2-yliden]-1,3,5-heptatrienyl]-3,3-dimethyl-1-(4-sulfobutyl)-3H-indolium, inner salt, potassium hydrogen salt according to known methods (*Cytometry* 11 (1990) 418-430).

0.16 g (1.22 mmol) of aspartic acid in 1 ml of DMF are added to a solution of 0.5 g (0.51 mmol) of the disuccinimidyl ester in 5 ml DMF. The reaction mixture is stirred at room temperature for 48 h. The product is precipitated by adding ether, purified on RP-18 (LiChroprep, 15-25 µ, $H_2O$:MeOH 99:1 to 1:1) and lyophilized. 0.27 g (51%) of product are gained after drying for 24 hours at 50° C./0.01 mbar.

Analysis:

| | | | | | |
|---|---|---|---|---|---|
| Calc.: C 54.43 | H 5.54 | N 5.40 | O 24.68 | S 6.18 | K 3.77 |
| Det.: C 54.04 | H 5.81 | N 5.22 | | S 6.13 | K 3.85 |

Example 2

Preparation of 2-[7-[5-[2-[(11-carboxy-2-oxo-1,4,7,10-tetraaza-4,7,10-tri(carboxymethyl)-1-andecyl)amino]-2-oxoethyl]-1,3-dihydro-3,3-dimethyl-1-ethyl-2H-indol-2-yliden]-1,3,5-heptatrienyl]-3,3-dimethyl-1-(4-sulfobutyl)-3H-indolium, inner salt.

43 mg (0.65 mmol) of 85% hydrazine hydrate in 1 ml of methanol are slowly added by dropping to a solution of 0.5 g (0.73 mmol) 2-[7-[5-(carboxymethyl)-1,3-dihydro-3,3-dimethyl-1-ethyl-2H-indol-2-yliden]-1,3,5-hepta-trienyl]-3,3-dimethyl-1-(4-sulfobutyl)-3H-indolium-N-succinimidyl ester, inner salt in 5 ml of methanol (*Cytometry* 11 (1990) 418-430) at −10° C. and stirred for 2 hours at this temperature. The reaction mixture is evaporated under a vacuum to approx. 3 ml mixed with 1 ml of isopropanol and kept overnight at −20° C. The crystals that precipitate are sucked off and dried using the oil pump. The yield is 0.27 g (61%) of tricarbocyanine carbonic acid hydrazide.

0.27 g (0.45 mmol) of the hydrazide is added under stirring to a solution of 0.21 g (0.51 mmol) of diethylene triamine pentaacetic monoethyl ester monoanhydride in 20 ml DMF and 0.2 ml triethylamine. The mixture is kept agitated at room temperature for 48 hours. The solvent is evaporated at 0.2 mbar after filtering, the residue is mixed up with $CH_2Cl_2$, filtered off, and dried under high vacuum. The product gained is stirred up in 5 ml of 3 M aqueous NaOH at room temperature for 4 hours. Then, a pH value of 2.0 is set using semi-concentrated HCl. 1 ml of isopropanol is added. After allowing the mixture to stand at 4° C. for 18 hours, crystals that have precipitated are sucked off and dried under high vacuum at 60° C. for 24 hours.

Yield: 0.23 g (52%) of granulate that glimmers dark red.

Analysis:

| Calc.: | C 59.32 | H 6.60 | N 9.88 | O 20.96 | S 3.23 |
| --- | --- | --- | --- | --- | --- |
| Det.: | C 54.15 | H 6.70 | N 9.50 | | S 3.19 |

Example 3

Preparation of 2-[7-[1,3-dihydro-3,3-dimethyl-5-[2-[(methoxypolyoxyethylene)amino]-2-oxoethyl]-1-(4-sulfobutyl)-2H-indol-2-yliden]-1,3,5-heptatrienyl]-3,3-dimethyl-5-[2-[(methoxypolyoxyethylene)amino-2-oxoethyl]-1-(4-sulfobutyl)-3H-indolium, sodium salt.

A solution of 0.08 mmol of the N,N-disuccinimidyl ester from Example 1 in 1 ml of DMF is added to a solution of 800 mg of methoxypolyoxyethylene amine (ca. 0.16 mmol; average molar weight ca. 5000) in 10 ml of CH$_2$Cl$_2$ and kept agitated at room temperature for 24 hours. The solid product that precipitates after adding ether is filtered off and purified by chromatography (Sephadex G5O medium, H$_2$O as eluent), yield approx. 58% of green-blue powder after lyophilization and drying above P$_2$O$_5$.

Average molar weight calc.: 10771, det.: 10820.

Example 4

Preparation of 2-[7-[1,3-dihydro-3,3-dimethyl-1-(4-sulfobutyl)-2H-indol-2-yliden]-1,3,5-heptatrienyl]-3,3-dimethyl-5-(methoxypolyoxyethylene)aminocarbonyl-1-(4-sulfobutyl)-3H-indolium, sodium salt.

0.41 g (0.5 mmol) of 2-[7-[1,3-dihydro-3,3-dimethyl-1-(4-sulfobutyl-1-(4-sulfobutyl)-2H-indol-2-yliden]-1,3,5-hepatrienyl]-3,3-dimethyl-5-carboxy-1-(4-sulfobutyl)-3H-indolium-N-succinimidyl ester, sodium salt are stirred in an argon atmosphere together with 2.3 g of methoxy polyoxyethylene amine (0.46 mmol; average molar weight: 5000) in 70 ml CH$_2$Cl$_2$ at room temperature for 18 hours. The solvent is reduced by half under vacuum and the product is isolated as described in Example 3. The yield is 2.1 g of product in the form of a green blue powder.

Average molar weight calc.: 5701, det.: 5795.

Example 5

Preparation of 3-(3-carboxypropyl)-2-[7-[3-(3-carboxypropyl)-1,3-dihydro-3-methyl-1-(4-sulfobutyl)-2H-indol-2-yliden]-1,3,5-heptatrienyl]-3-methyl-1-(4-sulfobutyl)-3H-indolium, sodium salt.

6.5 g (50 mmol) of phenylhydrazine hydrochloride and 8.7 g (55 mmol) of 5-methyl-6-oxoheptanoic acid are stirred in 50 ml of concentrated acetic acid at room temperature for 1 hour, and at 120° C. for 5 hours. After reducing by evaporation, the residue is mixed up with 20 ml of water, and the crystals that have precipitated are filtered off and dried using the oil pump.

This yields 9.6 g (83%) of brownish crystals that are suspended in 60 ml of dichlorobenzene and, after adding 11.6 g (85 mmol) of 1,4-butane sultone, heated for 8 hours to 150° C. After the mixture has cooled down to room temperature, 200 ml of acetone are added, and the precipitate is filtered off. It is suspended in ether, filtered off again after 18 hours of stirring, and dried using the oil pump. The yield is 10.7 g (70%) of 3-(3-carboxypropyl)-2,3-dimethyl-1-(4-sulfobutyl)-3H-indolenin which is purified by chromatography (RP-18, LiChroprep, 15-25 µ, MeOH:H$_2$O as eluent).

The indotricarbocyanine dye is prepared by heating 5.0 g (13.6 mmol) of indolenin and 1.9 g (6.8 mmol) of glutaconaldehyde dianilhydrochloride in 100 ml of acetic anhydride for 30 minutes to 120° C., while adding 25 ml of conc. acetic acid and 2.3 g (27.6 mmol) of anhydrous sodium acetate. 500 ml of ether are added to the precipitate gained which is purified by chromatography (in portions of 1.0 g, RP-18, LiChroprep, 15-25 µ, MeOH:H$_2$O as eluent) and finally lyophilized. The yield is 2.5 g (45%) of the final product.

Analysis:

| Calc.: | C 60.13 | H 6.28 | N 3.42 | O 19.54 | S 7.83 | Na 2.81 |
| --- | --- | --- | --- | --- | --- | --- |
| Det.: | C 59.90 | H 6.34 | N 3.39 | | S 7.72 | Na 2.78 |

Example 6

Preparation of 2-[[3-[[3-(carboxypropyl)-1,3-dihydro-3-methyl-1-(4-sulfobutyl)2H-indol-2-yliden]methyl]2-hydroxy-4-oxo-2-cyclobuten-1-yliden]methyl]-1,1-dimethyl-3-ethyl-1H-benz(e)indolium, inner salt.

3.65 g (10.0 mmol) of 3-ethyl-1,1,2-trimethyl-lH-benz(e)indoliumiodide are added to a solution of 1.36 g (8.0 mmol) squaric diethyl ester and 1.6 ml triethylamine in 12 ml of ethanol that is heated up to 70° C. After 10 minutes of stirring at 80° C., the mixture is cooled down to 0° C. The precipitated, red-coloured crystals are filtered off, washed with ether, and dried under vacuum. Purification by chromatography on silica gel (CH$_2$Cl$_2$:AcOH 9:1 to 7:3) yields 1.33 g (46%) of 2-ethoxy-1-[(3-ethyl-1,1-dimethyl-1H-benz(e)indol-2-yliden)-methyl]-cyclobuten-3,4-dion.

This substance is suspended in 15 ml of boiling ethanol and mixed under stirring with 0.5 ml of 40% NaOH. The solution gained is stirred for 5 minutes at 80° C. and mixed with 5 ml of 2N HCl after cooling down to room temperature. The 1-[(3-ethyl-1,1-dimethyl-1H-benz(e)indol-2-yliden)-methyl]-2-hydroxycyclobutene-3,4-dion (1.30 g) that precipitates after evaporating is filtered, dried and used for the next step of synthesis without being purified.

The squarain dye is prepared by reacting 1.30 g (3.9 mmol) of the squaric acid derivative gained with 1.43 g (3.9 mmol)of 3-(3-carboxypropyl)-2,3-dimethyl-1-(4-sulfobutyl)-3H-indolenin. The components obtained are heated for 18 hours in 80 ml of toluene and 80 ml 1-butanol at the water separator and then freed from solvents under vacuum. The residue is mixed with ether, and the crystals that have formed are filtered off after 16 hours of stirring at room temperature, and purified by chromatography (RP-18, LiChroprep, 15-25 µ, MeOH:H$_2$O as eluent), yield: 0.95 g (36%).

Analysis:

| Calc.: | C 68.60 | H 6.20 | N 4.10 | O 16.40 | S 4.70 |
| --- | --- | --- | --- | --- | --- |
| Det.: | C 68.25 | H 6.35 | N 4.04 | | S 4.59 |

Example 7

Preparation of 2-[7-[1,3-dihydro-5-[2-[(2,3-dihydroxypropyl)amino]-2-oxoethyl]-3,3-dimethyl-1-(4-sulfobutyl)-2H-indol-2-yliden]-1,3,5-heptatrienyl]-5-[2-[(2,3-dihydroxypropyl)amino]-2-oxoethyl]-3,3-dimethyl-1-(4-sulfobutyl)-3H-indolium, sodium salt.

2.0 g (6.4 mmol) of 2,3,3-trimethyl-3H-indol-5-yl acetic succinimidyl ester in 50 ml $CH_2Cl_2$ are mixed with 0.84 g (6.4 mmol) of 4-aminomethyl-2,2-dimethyl-1,3-dioxolane. After 5 hours of stirring at room temperature, the mixture is poured on 100 ml of water and extracted with $CH_2CL_2$; the organic phases are evaporated. After chromatographic purification (silica gel $CH_2Cl_2$:MeOH 98:2) 1.86 g (88%) of the amide are gained which are stirred for 12 hours in 20 ml of dichlorobenzene and 1.36 g (10.0 mmol) of 1,4-butane sultone at room temperature, and at 100° C. The granulate that is formed after stirring the mixture up with 50 ml of acetone is filtered off and purified by chromatography (RP-18, LiChroprep, 15-25 μ, MeOH:$H_2O$ as eluent). The yield is 0.85 g (28% referred to the parent compound) of 5-[2-[(2,2-dimethyl-1,3-dioxa-4-cyclopentyl)methyl]amino-2-oxoethyl]-2,3,3-trimethyl-1-(4-sulfobutyl)-3H-indolenin.

The reaction to produce the dye is similar to Example 4. The substance is heated for 10 minutes to 120° C. The crude product is stirred at room temperature in 5 ml MeOH by adding 100 mg toluene-p-sulfonic acid for 16 hours; insoluble parts are separated. The filtrate is then kept at −20° C. after adding 3 ml of isopropanol. The powder that precipitates is purified by chromatography (RP-18, LiChroprep, 15-25 μ, MeOH:$H_2O$ as eluent), lyophilized and dried for 24 hours at 50° C./0.01 mbar. Yield: 0.32 g (37%).

Analysis:

| | | | | | | |
|---|---|---|---|---|---|---|
| Calc.: | C 56.70 | H 6.45 | N 5.88 | O 20.14 | S 6.73 | K 4.10 |
| Det.: | C 56.39 | H 6.88 | N 5.67 | | S 6.58 | K 3.93 |

Example 8

2-[7-[1,3-dihydro-3,3-dimethyl-5-(methoxycarbonyl)-1-(4-sulfobutyl)-2H-indol-2-yliden]-1,3,5-heptatrienyl]-3,3-dimethyl-5-(methoxycarbonyl)-1-(4-sulfobutyl)-3H-indolium, sodium salt at a dose of 3.8 μmol/kg body weight was applied intravenously to an anaesthetized, tumour-bearing mouse (Swiss Nude; tumour LS 174 T at the right hindleg).

The laser-induced fluorescent images were taken prior to, and at various points in time after, applying the substance with a fluorescence imager (at Physikalisch-Technische Bundesanstalt, Berlin Charlottenburg). Radiation was excited using monochromatic laser light at 740 nm by decoupling the radiation via a fibre optical waveguide system. Exciting radiation below 740 nm was removed using a cutoff filter. The laser-induced fluorescence light above 740 nm was recorded using a CCD camera (Charge Coupled Device), and data was stored in the form of black-and-white images.

The sequence of shots shown in FIG. 1 clearly shows a general increase of fluorescent intensity after the substance was applied (A, B). A uniform distribution of intensity can be observed after 30 seconds, with values being increased in the hepatic and pulmonary regions and in the tumour (B). With more time elapsing (up to 1 h) (C, D, E), the substance spreads more and more throughout the animal. After 18 hours, a clearly increased fluorescent intensity can be observed in the tumour (right hindleg) as compared with the rest of the body.

FIG. 1 shows fluorescent light images (black-and-white) of a mouse (Swiss Nude) at various points in time after i.v. application of 3.8 mmol/kg body weight of 2-[7-[1,3-dihydro-3,3-dimethyl-5-(methoxycarbonyl)-1-(4-sulfobutyl)-2H-indol-2-yliden]-1,3,5-heptatrienyl]-3,3-dimethyl-5-(methoxycarbonyl)-1-(4-sulfobutyl)-3H-indolium, sodium salt.

A-E: right lateral images, F: posterior image
A: prior to application,
B: 30 secs,
C: 1 min,
D: 10 mins,
E: 1 h after application,
F: 18 h after application.

What is claimed is:

1. An in-vivo diagnostic based on near infrared radiation comprising compounds of the general formula I

wherein
L represents a number from 0 to 6,
n represents a number from 0 to 10, and
m represents a number from 1 to 100;
B is a biological detecting unit having a molecular weight of up to 30,000 that bonds to specific cell populations or selectively to receptors, or accumulates in tissues or tumours, or generally stays in the blood, or is a macromolecule that bonds non-selectively;
F represents a dye showing maximum absorption in the range of 650 to 1200 nm;
as well as their physiologically tolerable salts, wherein F within the general formula I represents a cyanine dye of the general formula IIa

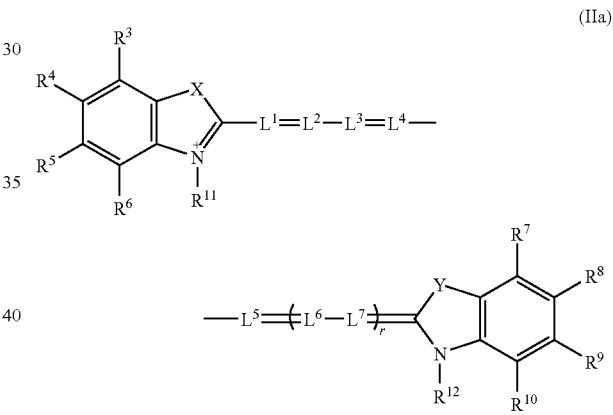

wherein
r represents the numbers 0, 1 or 2, wherein, for r=2, the respective $L^6$ and $L^7$ groups that occur in duplicate may be the same or different, $L^1$ to $L^7$ are the same or different, each independently representing a CH or CR group, where
R is a halogen atom, a hydroxy, carboxy, acetoxy, amino, nitro, cyano or sulfonic acid group or an alkyl, alkenyl, hydroxyalkyl, carboxyalkyl, alkoxy, alkoxycarbonyl, sulfoalkyl, alkylamino, dialkylamino or halogenalkyl group containing up to 6 carbon atoms, an aryl, alkylaryl, hydroxyaryl, carboxyaryl, sulfoaryl, arylamino, diarylamino, nitroaryl or halogenaryl group containing up to 9 carbon atoms, or where R represents a bond that bonds to another group R and forms a 4- to 6-member ring together with the interspersed groups $L^1$ to $L^7$, or two of $L^1$ to $L^7$ that are linked via a —CO— group,
$R^3$ to $R^{12}$ are the same or different, each independently representing a hydrogen atom, a group B as defined above or W as defined below, or an alkyl or alkenyl group containing up to 6 carbon atoms or an aryl or aralkyl group optionally carrying an additional group W as defined below, or with 5- to 6- member rings that may be saturated, unsaturated or aromatic, and that may optionally carry an additional group R as defined above, annealed to each pair of adjacent residue $R^3$ to $R^{10}$ with due regard for the interspersed C atoms, X and Y are the same or different, each independently representing an O, S, Se or Te or a —$C(CH_3)_2$—, —CH=CH— or —$CR^{13}R^{14}$— group, where $R^{13}$ and $R^{14}$ independently represent a hydrogen atom, a group B as defined above or W as defined below, or an alkyl or alkenyl group containing up to 6 carbon atoms or an aryl or aralkyl group containing up to 9 carbon atoms, the alkyl, alkenyl, aryl or aralkyl group optionally carrying an additional group W as defined below, wherein W within the general formula I is a carboxy or sulfonic acid group or a carboxyalkyl group or an alkoxycarbonyl or alkoxyoxoalkyl group containing up to 12 carbon atoms, and wherein W takes the position of $R^4$ and $R^8$, $R^6$ and $R^{10}$, $R^{11}$ and $R^{12}$, or combinations thereof.

2. A method of producing a fluorescent image in tissues, the method comprising administering at least one of the compounds of claim 1 to tissues and detecting said compound by means of near infrared radiation.

3. An agent for in-vivo diagnosis comprising at least one of the cyanine dyes according to claim 1 together with common adjuvants, substrates and diluents.

\* \* \* \* \*

UNITED STATES PATENT AND TRADEMARK OFFICE
CERTIFICATE OF CORRECTION

PATENT NO. : 7,655,217 B2
APPLICATION NO. : 11/387367
DATED : February 2, 2010
INVENTOR(S) : Licha et al.

It is certified that error appears in the above-identified patent and that said Letters Patent is hereby corrected as shown below:

Column 18, Line 15, Claim 1, "from 0 to 10" should read -- from 1 to 10 --

Signed and Sealed this

Twentieth Day of April, 2010

David J. Kappos
*Director of the United States Patent and Trademark Office*